United States Patent
Benea et al.

(10) Patent No.: US 7,275,446 B2
(45) Date of Patent: Oct. 2, 2007

(54) APPARATUS FOR MEASURING THE CRUSHING STRENGTH OF MICRON SUPERABRASIVES

(75) Inventors: Ion Benea, Wheeling, IL (US); Stephen Griffin, Elk Grove Village, IL (US); Ralph Doyle, Palatine, IL (US)

(73) Assignee: Engis Corporation, Wheeling, IL (US)

( * ) Notice: Subject to any disclaimer, the term of this patent is extended or adjusted under 35 U.S.C. 154(b) by 129 days.

(21) Appl. No.: 10/565,123

(22) PCT Filed: Jul. 20, 2004

(86) PCT No.: PCT/US2004/023116

§ 371 (c)(1), (2), (4) Date: Jan. 19, 2006

(87) PCT Pub. No.: WO2005/009680

PCT Pub. Date: Feb. 3, 2005

(65) Prior Publication Data

US 2006/0174714 A1    Aug. 10, 2006

Related U.S. Application Data

(60) Provisional application No. 60/489,111, filed on Jul. 23, 2003.

(51) Int. Cl.
G01N 3/08    (2006.01)
(52) U.S. Cl. ....................................... 73/824
(58) Field of Classification Search ............. 73/824
See application file for complete search history.

(56) References Cited

U.S. PATENT DOCUMENTS

| 2,224,248 A | * | 12/1940 | Blum et al. .................... 73/821 |
| 2,518,959 A | * | 8/1950 | Tinker ......................... 73/821 |
| 3,713,592 A | | 1/1973 | Beike et al. |
| 3,831,437 A | | 8/1974 | Sheets et al. |
| 3,994,157 A | * | 11/1976 | Burk et al. .................... 73/806 |
| 4,054,050 A | * | 10/1977 | Reid ........................... 73/806 |
| 4,581,253 A | * | 4/1986 | Evans et al. ................. 427/221 |
| 5,402,366 A | | 3/1995 | Kihara et al. |
| 5,454,260 A | | 10/1995 | Wang |

* cited by examiner

*Primary Examiner*—Max Noori
(74) *Attorney, Agent, or Firm*—McDermott Will & Emery LLP

(57) ABSTRACT

A method and apparatus are provided for measuring the crushing strength of an abrasive, comprising particles, used in a lapping process. Embodiments include a crushing strength tester having a cup for holding the abrasive; a first motor for rotating the cup in a first direction; a piston having a face for rotatably fitting within the cup and contacting the abrasive; a second motor for rotating the piston in a second direction opposite the first direction; and a press for pressing the piston against the abrasive and crushing the particles while the first and second motors are rotating. An initial particle size distribution for the particles is determined, then the abrasive is subjected to a crushing force approximately equal to that of the lapping process using the crushing strength tester. A post-crushing particle size distribution for the particles is determined, and the initial and post-crushing particle size distributions are compared.

20 Claims, 6 Drawing Sheets

APPARATUS FOR MEASURING THE CRUSHING STRENGTH OF MICRON SUPERABRASIVES

RELATED APPLICATION

This application is the U.S. National Phase under 35 U.S.C. § 371 of International Application No. PCT/US2004/023116, filed on Jul. 20, 2004, which in turn claims the benefit of U.S. Provisional Patent Application No. 60/489,111, filed on Jul. 23, 2003, the disclosure of which Applications are incorporated by reference herein.

FIELD OF THE INVENTION

The present invention relates to the characterization of micron superabrasives with respect to mechanical strength and fracture characteristics. The present invention has particular applicability in measuring the crushing strength of micron superabrasive powders used; e.g., in lapping processes.

BACKGROUND ART

It is well known that the fracture mechanism of micron superabrasive powders, defined as diamond and cubic boron nitride (CBN) powders, plays a determinant role in the abrasive process. The fracture mechanism of superabrasive particles is controlled by their crystalline structure (i.e. monocrystalline vs. polycrystalline) and by the nature and concentration of crystal growth defects (i.e. pre-existing fractures, voids, mechanical stresses and impurities). Consistent abrasive performance is achieved only by employing micron superabrasive powders whose properties are precisely defined and controlled. Therefore, it is crucial that micron superabrasive powder products be designed and manufactured to possess a specific set of chemical and physical properties that are responsible for their performance in a particular application. It is equally important that the end user understand the chemical and physical properties associated with different micron superabrasive powder types/products, and make an informed decision to select the product that performs best for their application. Whether used as abrasive or non-abrasive (i.e. feedstock for PCD manufacturing), mechanical strength and fracture characteristics are primarily responsible for the performance of a micron superabrasive powder type/product.

Generally, sub-sieve powders (powders that are smaller than 400 mesh) are considered micron powders. However, in the size range from 40 microns (approx. 400 mesh) to 80 microns (approx. 200 mesh), fine mesh sizes overlap with coarse micron-sizes. It is well known that the fracture mechanism of micron superabrasive particles plays a determinant role in any abrasive process. During abrasive action, the edges and points of micron superabrasive particles tend to dull. Progressive dulling of the particles leads to increased mechanical and thermal stresses at the abrasive-workpiece interface. If allowed to continue, this process leads to catastrophic failure of the micron superabrasive particles and workpiece damage. To avoid catastrophic failure, the micron superabrasive particles must be able to microfracture under severe mechanical stresses and develop new fresh cutting edges and points in a so-called "self sharpening" mechanism.

The fracture mechanism of micron superabrasive particles is controlled by crystalline structure (i.e. monocrystalline vs. polycrystalline) and by the nature and concentration of crystal growth defects (i.e. pre-existing fractures, voids, mechanical stresses and impurities). Virtually all synthetic mesh micron superabrasive powders are commercially produced via the catalytic high pressure-high temperature (HPHT) synthesis process. Manufacturing of micron superabrasive powders by the same process has been proven difficult, impractical and expensive. Micron superabrasive powders represent a by-product of the diamond or CBN synthesis process and are produced by milling of mesh size powders. Consequently, some of the characteristics of the starting mesh powders (so-called diamond or CBN feeds), are mirrored in the resulting micron superabrasive powders.

The intrinsic properties of the diamond or CBN crystal are determined by the nature (static vs. dynamic) and particularities of the HPHT synthesis process. For a given graphite-catalyst system, the kinetics of the catalytic HPHT synthesis process (i.e., nucleation and growth rates) is controlled by thermodynamic parameters—pressure and temperature. Furthermore, the nucleation and growth rates control the nature and amount of crystal growth defects (pre-existing fractures, voids, mechanical stresses, impurities) which, in turn, are responsible for the mechanical strength of the crystal. Therefore, there is a direct relationship between the crystal characteristics (size, shape, mechanical strength) and the nucleation and growth rates, as follows:

Low nucleation and growth rates produce larger, well developed (regular shaped) crystals with a low level of crystal growth defects and high mechanical strength.

High nucleation and growth rates produce smaller, poorly developed (irregular shaped) crystals with a high level of crystal growth defects and low mechanical strength.

As a general rule, the level of crystal growth defects is strongly related to the synthesis process, while the distribution of crystal strength within the population is related to the post-synthesis processing of mesh powders (shape sorting, magnetic separation, etc). A brief summary of the particularities of some of the most frequently practiced catalytic HPHT diamond synthesis processes is presented in Table 1.

TABLE 1

| | Belt, Press | | Cubic/ Hexagonal | Apposed Anvils |
|---|---|---|---|---|
| HPHT Device | Straight | Curved | Press | Press |
| Metal Catalyst | Ni—Fe | Co—Fe Ni—Fe | Ni—Co—Mn | Ni—Mn |
| Graphite-Metal charge | Discs/Powder | | Discs/Powder | Powder |
| HPHT cycle | Long-Moderate | | Moderate-Short | Short-V. Short |
| Growth rate | Low-Moderate | | Moderate-High | High-V. High |
| Crystal growth defects | Low-Moderate | | Moderate-High | High-V. High |

The characterization of micron superabrasive powders is a difficult and complex task, involving the evaluation of the properties of a very large number of particles. There are no standard techniques in the prior art for measuring the mechanical strength and/or fracture characteristics of micron superabrasive powders, by either static or dynamic methods. Instead, the mechanical strength and fracture characteristics of micron superabrasive powders are controlled indirectly, by controlling the feed type and quality (i.e., metal bond diamond/CBN using a belt press or cubic press synthesis process; or resin bond diamond/CBN using a belt press or cubic press or opposed anvils press synthesis process). Furthermore, the concentration of residual crystal growth defects, as well as the particle shape and surface texture of the resulting micron superabrasive powders, can be significantly modified through a number of mechanical, chemical and thermal processes that are incorporated into the micronizing process.

There exists a need for a methodology and apparatus for characterization of different micron superabrasive powder types/products with respect to fracture strength and fracture characteristics.

SUMMARY OF THE INVENTION

An advantage of the present invention is a method and apparatus for the characterization of micron superabrasive powder types and/or products with respect to mechanical strength and fracture characteristics based on an evaluation of their fracture strength and fracture characteristics (mode of fracture) when subjected to mechanical forces similar to those encountered in lapping processes.

According to the present invention, the foregoing and other advantages are achieved in part by a method for measuring the crushing strength of an abrasive comprising particles, used in a lapping process. The method comprises determining an initial particle size distribution for the particles; subjecting the abrasive to a crushing force approximately equal to that of the lapping process; determining a post-crushing particle size distribution for the particles; and comparing the initial and post-crushing particle size distributions.

Another aspect of the present invention is an apparatus for measuring the crushing strength of an abrasive, comprising particles, used in a lapping process. The apparatus comprises a cup for holding the abrasive; a first motor for rotating the cup in a first direction; a piston having a face for rotatably fitting within the cup and contacting the abrasive; a second motor for rotating the piston in a second direction opposite the first direction; and a press for pressing the piston against the abrasive and crushing the particles while the first and second motors are rotating.

Additional advantages of the present invention will become readily apparent to those skilled in this art from the following detailed description, wherein only one exemplary embodiment of the present invention is shown and described, simply by way of illustration of the best mode contemplated for carrying out the present invention. As will be realized, the present invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein.

DESCRIPTION OF THE INVENTION

The present invention represents a breakthrough in the characterization of micron superabrasives (i.e., diamond and CBN powders) with respect to fracture strength, a property that is ultimately responsible for their performance in most application areas. The inventive apparatus measures the fracture strength of micron superabrasives when subjected to crushing action under controlled conditions that replicate lapping process conditions.

The present invention includes an apparatus and a measurement technique to characterize micron superabrasive powder types or products with respect to their fracture strength, expressed as crushing strength or resistance to crushing. The measurement technique is based on the evaluation of the ratio of particles that resisted crushing to the initial number of particles (before crushing) in a given micron superabrasive powder, when subjected to mechanical forces similar to those encountered in the lapping process.

The inventive crushing strength technique makes possible direct and reliable comparisons between different micron superabrasives types or products with respect to their crushing strength.

Figure 1:
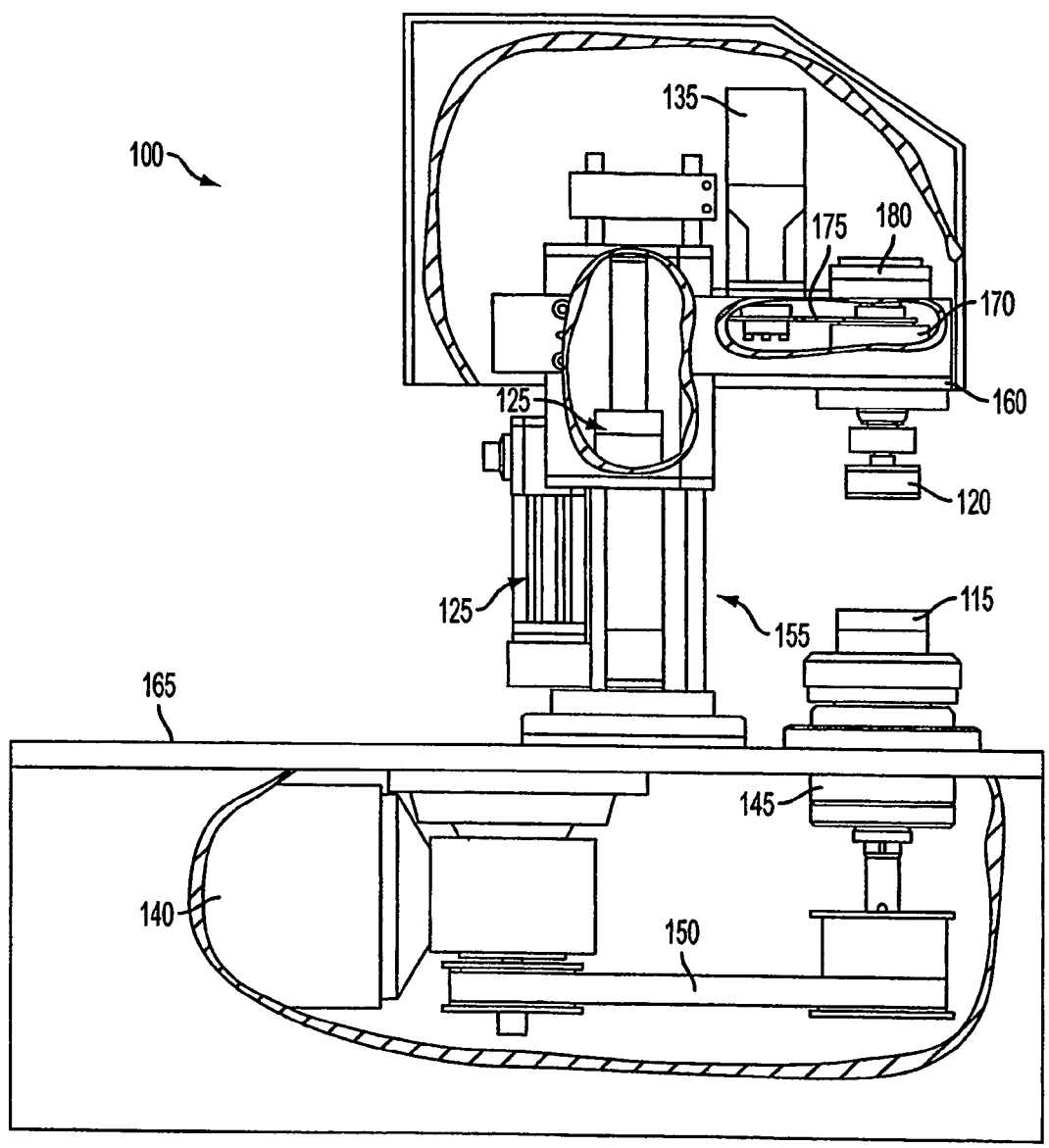
FIG. 1 schematically illustrates an apparatus for measuring crushing strength of micron superabrasives in accordance with an embodiment of the present invention.

An apparatus according to an embodiment of the present invention will now be described with reference to FIG. 1. Testing machine 100 uses lapping process kinematics to crush micron superabrasive powders under controlled conditions, in a size range down to 10 microns (mean size of the particle size distribution). A capsule 110 for crushing the superabrasive powders under test comprises a steel cup 115 and a steel piston 120 which rotate independently in opposite directions at controlled speeds by gearmotors 135, 140, the speeds being measured in revolutions per minute (RPM). The rotation speeds of both the cup and the piston can be varied from a few RPM to 200 RPM. A linear actuator 125, such as a conventional double end hollow rod pneumatic or hydraulic cylinder, or a conventional servo-driven actuator, is connected to piston 120 to deliver the desired loads (e.g., 500 lbs or less) to cup 115, which is rotatably mounted to a spindle 145. Spindle 145 is connected to gearmotor 140 via a belt 150, and piston 120 is rotatably coupled to spindle 170, which is connected to gearmotor 135 via chain 175. Gearmotor 135 is rigidly mounted to an anti-rotation assembly 155. Piston 120, linear actuator 125, anti-rotation assembly 155, gearmotor 135 and spindle 170 are all rigidly mounted to a platform 160. Cup 115, spindle 145, gearmotor 140 and anti-rotation assembly 155 are all rigidly supported by a base 165.

Figure 2:
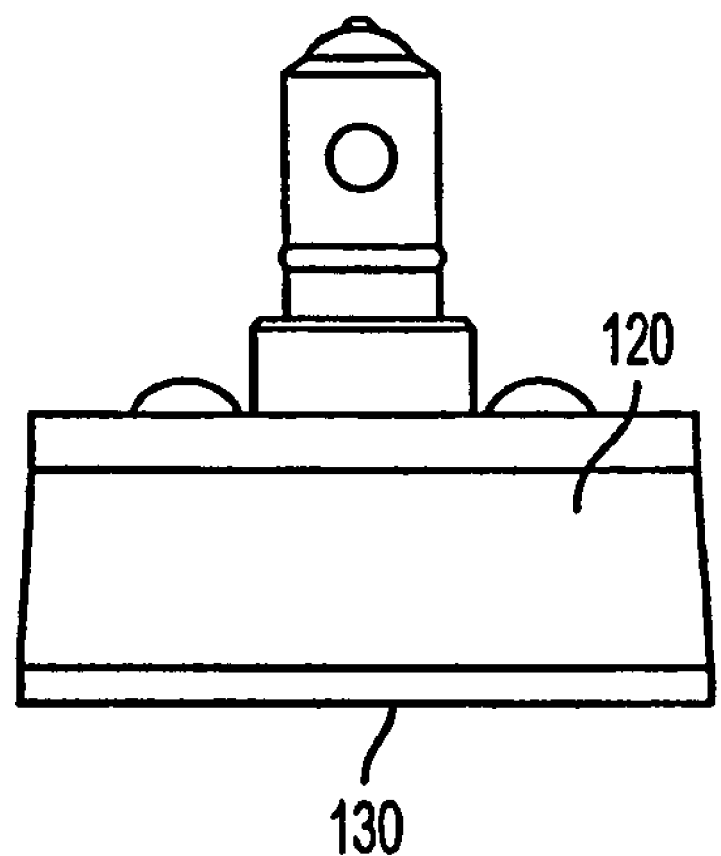
FIG. 2 is a cross-sectional view of a portion of the apparatus of FIG. 1.
Figure 2:
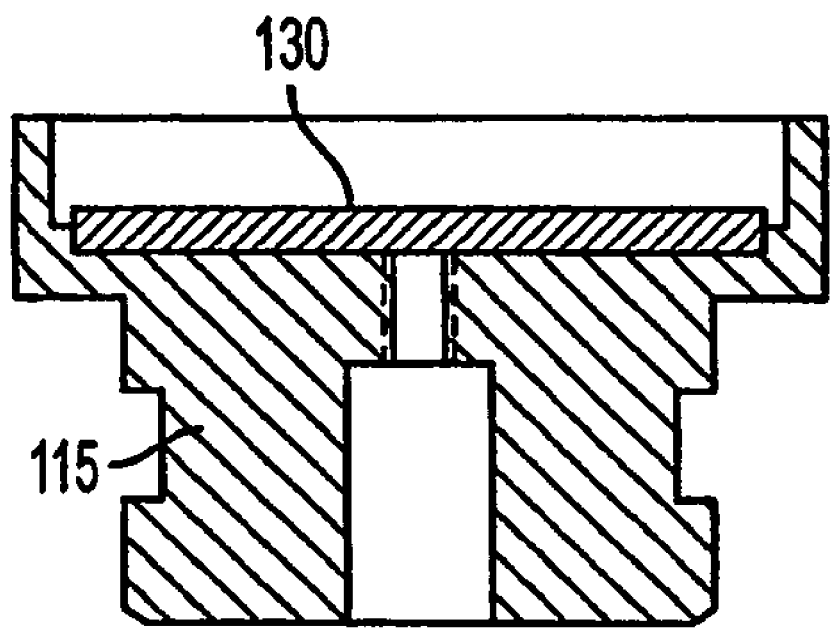

Referring now to FIG. 2, both the face 120a of piston 120 and the bottom 115a of cup 115 are lined with polycrystalline diamond compact (PCD) discs 130 to prevent contamination of the superabrasive powders during crushing due to erosion of the steel parts and, at the same time, to ensure precision and consistency of the test results. Thus, the micron superabrasive powders are crushed solely between the two PCD discs 130, without contact with the steel parts.

Figure 7:
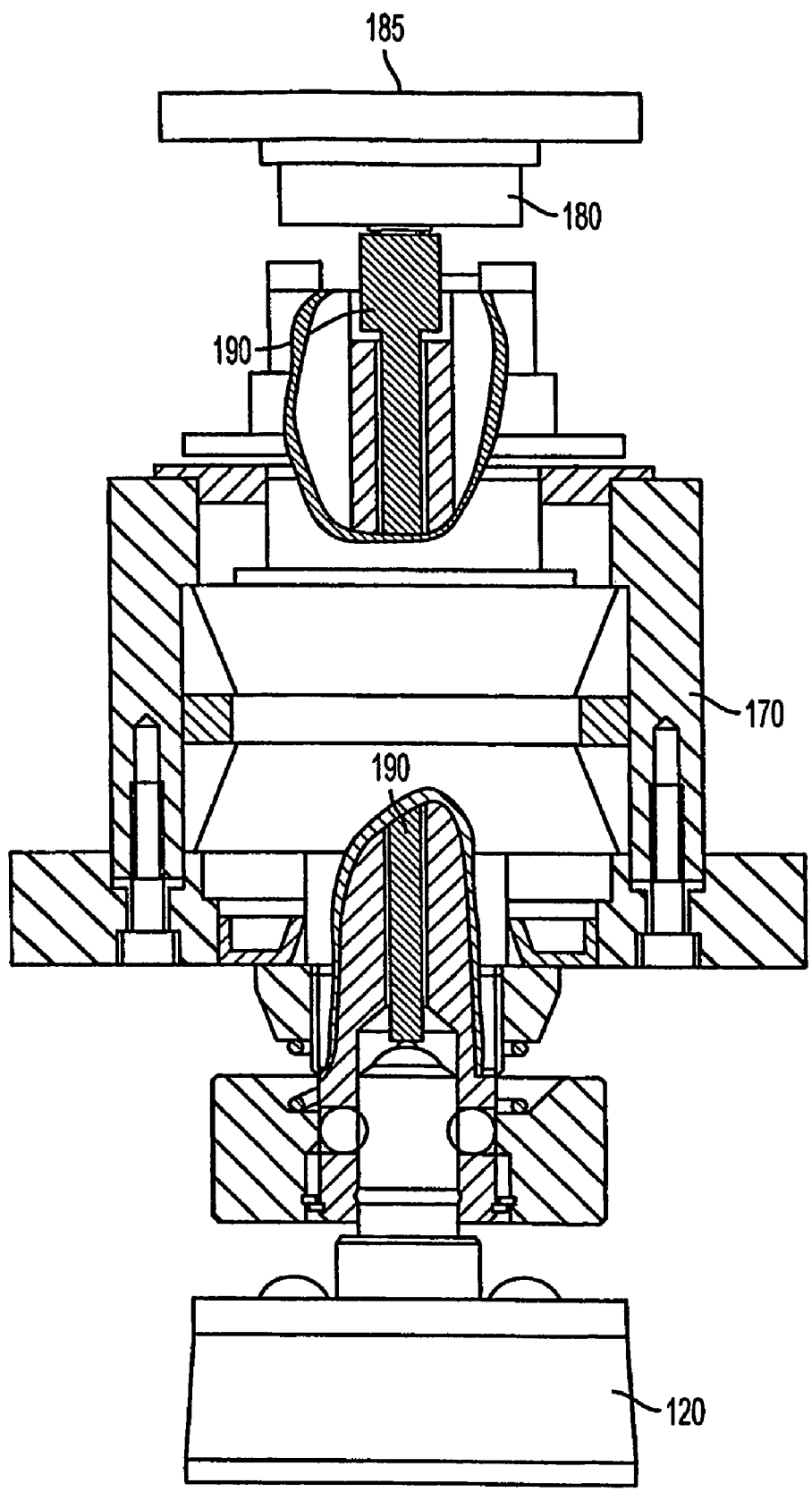
FIG. 7 is a cross-sectional view of a portion of the apparatus of FIG. 1.

Referring now to FIG. 7, when piston 120 mounted to spindle 170 makes contact with the superabrasives in cup 115, piston 120 pushes on a load transfer rod 190, which in turn presses against a conventional load cell 180 attached to a load cell mount 185, causing load cell 180 to produce a signal. The signal is sent to linear actuator 125 for interpretation to produce the preset desired force for crushing.

A crushing strength test cycle according to an embodiment of the present invention will now be described. A known amount (e.g., one carat) of micron superabrasive powder is charged into cup 115 on top of PCD disc 130 to form a circular layer of uniform thickness, and the crushing cycle is started. First, piston 120 is lowered into cup 115 until it touches the superabrasive powder layer. Next, the desired load is applied. Following a short period of time allowed for the load to be evenly applied over the entire area under piston 120 in contact with the superabrasive particles, both the cup 115 and the piston 120 are rotated simultaneously in opposite directions at the desired speeds, for the entire duration of the crushing cycle. After completion of the crushing cycle, the rotation of cup 115 and piston 120 is simultaneously stopped, the load is removed and the piston 120 is lifted. The a s-crushed micron superabrasive powder is then carefully collected into a glass beaker, by washing cup 115 and piston 120 with de-ionized (DI) water.

Crushing strength tests utilizing the above-described apparatus and techniques of an embodiment of the present invention will now be described. Prior to running crushing strength tests, the apparatus was calibrated with respect to applied load and the RPM of the cup and piston. As discussed above, the rotation speeds of both the cup and the piston can be varied from a few RPM to 200 RPM. However, the rotation speeds of both cup 115 and piston 120 are kept constant at 10 RPM throughout all crushing tests, except for during the static crushing experiments described below, where cup 115 and piston 120 were not rotated (i.e., RPM=0).

Figure 3A:
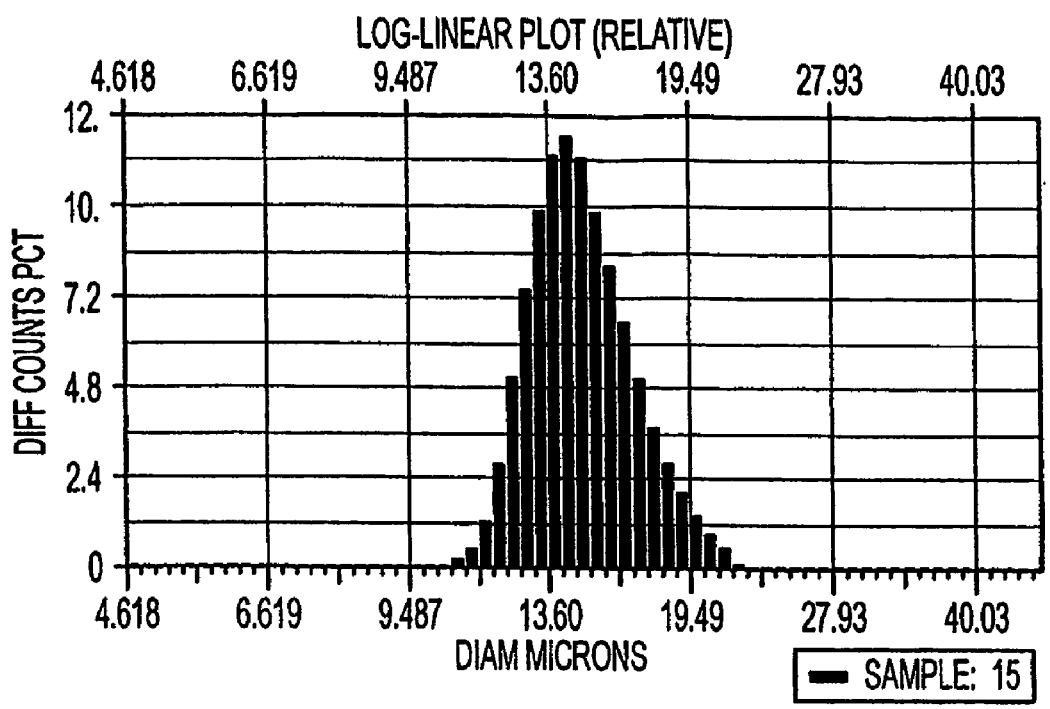
FIGS. 3A and 3B are graphs showing particle size distribution (PSD) for a superabrasive before and after crushing, respectively.
Figure 3B:
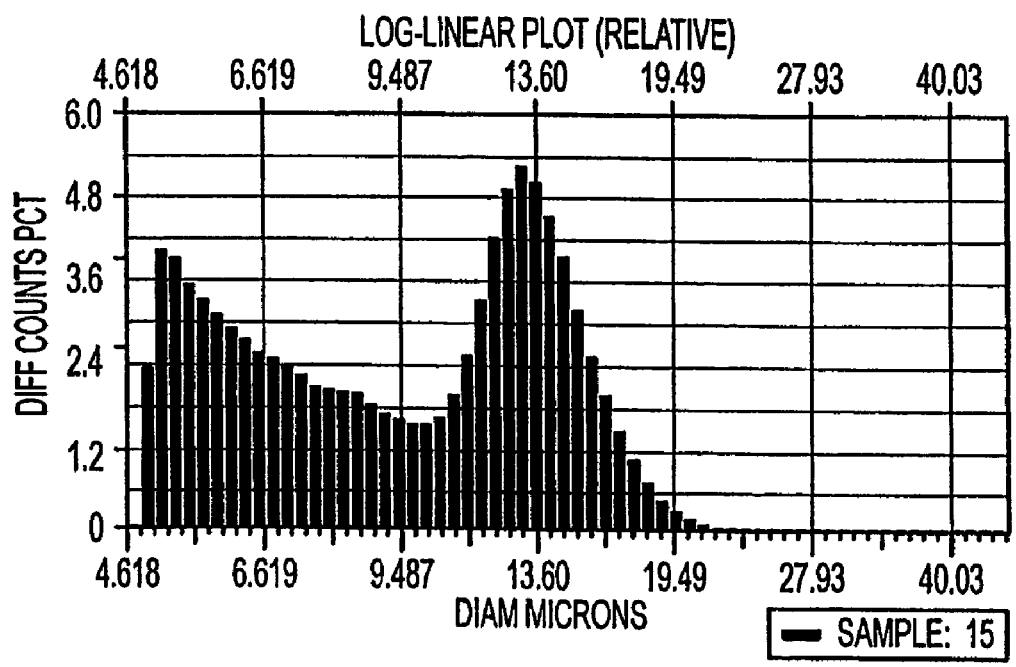

To determine the fracture (crushing) strength of the micron superabrasive powders under test, the particle size distributions (i.e., frequency distributions) of the original powders prior to crushing and of the resulting powders after crushing were measured using a conventional particle size distribution (PSD) analyzer, such as the Elzone 5382 analyzer. As an example, FIGS. 3A-B show the PSD of 10-20 μ MA superabrasive before and after crushing, respectively. The PSD data are used to calculate the crushing strength index of the micron powders. The product designations "MA", "RA" and "IG" used herein are explained in Table 2 below.

TABLE 2

| HPHT Process | Belt | Cubic | Opposed Anvils |
|---|---|---|---|
| Diamond type | Metal bond | Metal bond | Resin bond |
| Product designation | MA | IG | RA |
| Size (μ) | 20-40 | 20-40 | 20-40 |
| | 10-20 | 10-20 | 10-20 |
| | 8-12 | 8-12 | 8-12 |

The following test parameters are used to quantify the crushing strength of micron superabrasive powders tested according to the present invention:

On-size particles in the starting powder (OSS): The cumulative percentiles of particles between 50% and 95% of the frequency distribution, in the starting superabrasive powder (prior to crushing) is the OSS, On-size particles in the resulting powder (OSR): The cumulative percentiles of particles between 50% and 95% of the frequency distribution, in the resulting superabrasive powder (after crushing) is the OSR.

The crushing strength and crushing strength index are defined as follows:

Crushing strength is the ratio of the on-size particles in the resulting powder (particles that resisted crushing), to the on-size particles in the starting powder, Crushing strength index (CSI):

$$CSI = OSR/OSS \times 100$$

Prior to running the actual crushing strength tests, the following experiments were run to determine the optimum test parameters, and to assess the precision of the crushing strength measurement:

Static crushing (RPM=0; Time=1 min)

Crushing vs. time (Load=22.32 lb; Time=1.0, 1.5 and 2.0 min)

Crushing vs. load (Time=1 min, Load=13.4, 42.8, 60.8, and 81.0 lb)

Crushing test precision (Time=1 min, Load =13.4 lb, No. of runs per sample=5)

The sample matrix of Table 2 was used to investigate the crushing strength and fracture mode of different micron superabrasive powder types/products. The samples used in all crushing experiments were "as received" micron superabrasive powders and no further processing of the samples was performed, to preserve the intrinsic characteristics of each type/product. In addition, to prevent alteration of the test results by PSD variations from sample to sample, care was exercised to select substantially "identical" (i.e., as close as possible) particle size distributions for each micron superabrasive powder investigated. The particle size distribution data for each starting powder is presented in Table 3.

TABLE 3

PSD data of reference (un-crushed) micron superabrasive powder samples

| | Mean | 5% | 95% |
|---|---|---|---|
| 20-40 μ | | | |
| MA | 29.21 | 23.55 | 36.77 |
| IG | 30.10 | 24.60 | 37.58 |
| RA | 29.27 | 23.00 | 37.31 |
| 10-20 μ | | | |
| MA | 14.59 | 11.94 | 18.94 |
| IG | 16.44 | 11.80 | 21.26 |
| RA | 15.77 | 6.05 | 20.57 |
| 8-12 μ | | | |
| MA | 10.01 | 7.83 | 12.18 |
| IG | 10.13 | 8.18 | 12.13 |
| RA | 9.86 | 8.16 | 11.99 |

To qualitatively assess the fracture characteristics or fracture mode of micron superabrasive powders under investigation, the fine particles generated during the crushing test were first extracted (separated) from the as-crushed powders via conventional sedimentation. Following the separation step, the particle size distribution of each fine particles fraction was conventionally measured using, for example, the Horiba LB 500 analyzer (min. detection limit=3 nanometers; max. detection limit=6 microns). In addition, conventional scanning electron microscopy (SEM) and field emission scanning electron microscopy (FESEM) analysis was performed for 10-20μ and 8-12μ respectively, to understand the fracture behavior of the three micron superabrasive powder types/products MA, IG and RA.

Typical results of the calibration experiments will now be discussed. The distribution of the "on-size" particles in the as-crushed powders was plotted for 10-20μ MA subjected to static loading (compression). The data showed that under static compression and for the loads used, the micron superabrasive powder does not exhibit any significant (measurable) crushing.

The crushing of micron superabrasive particles vs. time, under constant load, was also studied. Under constant loading conditions, the ratio of the on-size particles in the resulting powder to the on-size particles in the starting powder, or crushing strength, decreases with time. In other words, for a given micron superabrasive powder there is a direct relationship between the extent of crushing and crushing time. To understand the relationship between particle crushing and load, a number of crushing experiments were conducted using a range of applied loads at constant time. While a measurable amount of crushing took place when the applied load was increased to 13.4 lb, there was very little crushing noticed when the load was further increased from 13.4 to 81.0 lb. These results are consistent with the results of the static crushing experiments indicating that, at least for the range of loads used in these experiments, micron superabrasive particles crush more under shear rather than compressive stresses.

The precision of crushing strength measurements obtained using the inventive apparatus and methodology was determined by running five post-calibration crushing experiments in a row under constant test conditions (Load=13.4 lb; time=1 min; RPM=10). The crushing experiments were conducted on 10-20μ MA, conventionally called "master diamond". The arithmetic mean and standard deviation for on-size particles in as-crushed powder (50% to 95% of the frequency distribution), as well as the crushing strength index, were calculated. The experimental results are presented in Table 5.

The above experimental data show that the crushing strength index of "master diamond" 10-20μ MA is 51.4+/31 1.1%, which indicates that the precision of the crushing strength measurement obtained using the present invention is better than 1.5%.

Figure 4:
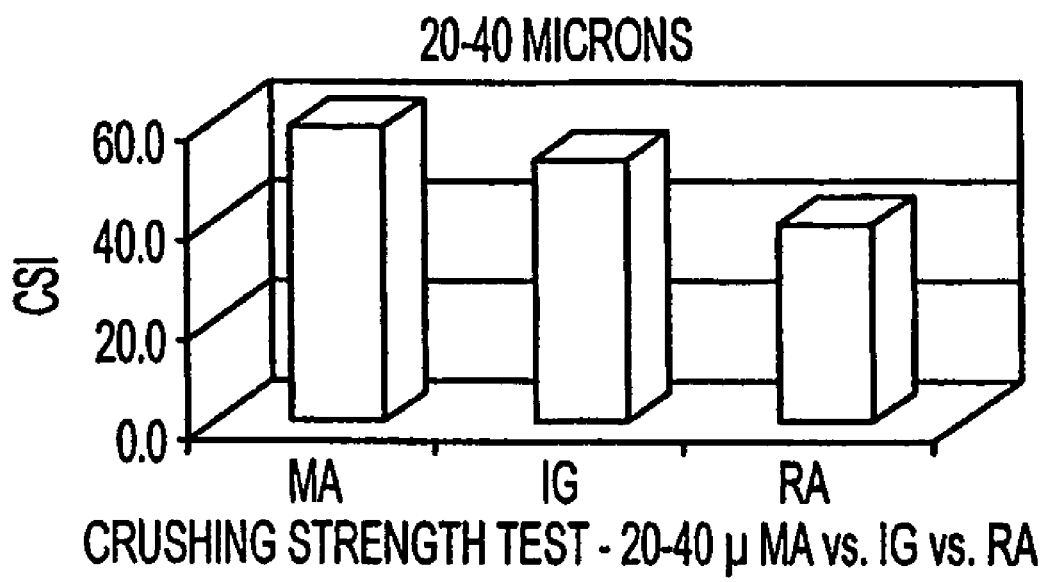
FIGS. 4-6 are graphs showing the crushing strengths of several superabrasives as obtained using the present invention.
Figure 5:
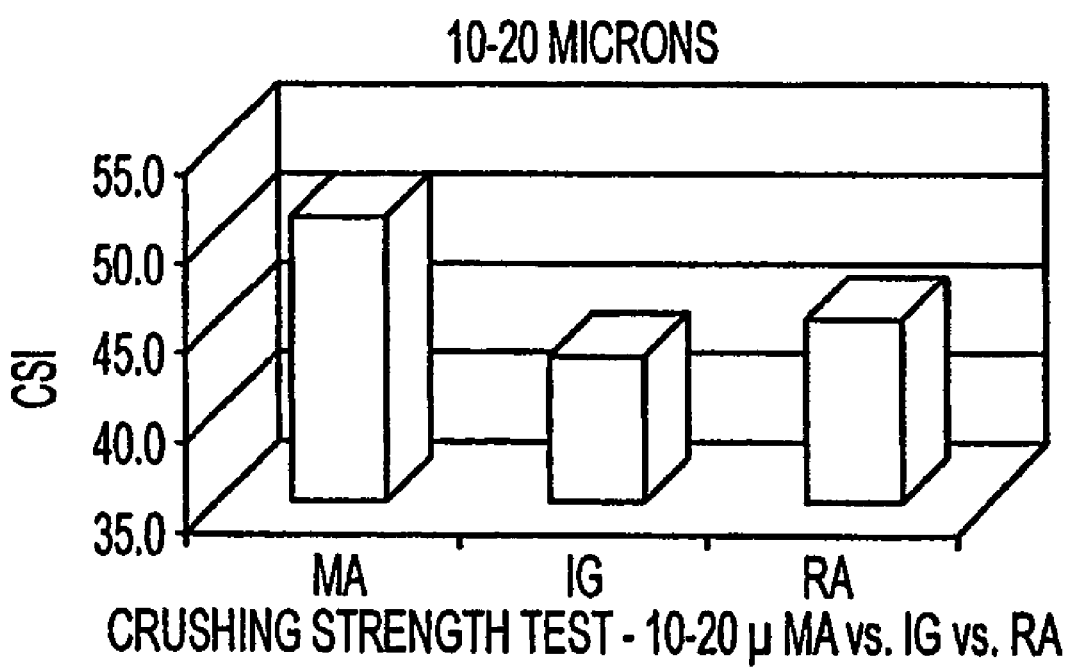
Figure 6:
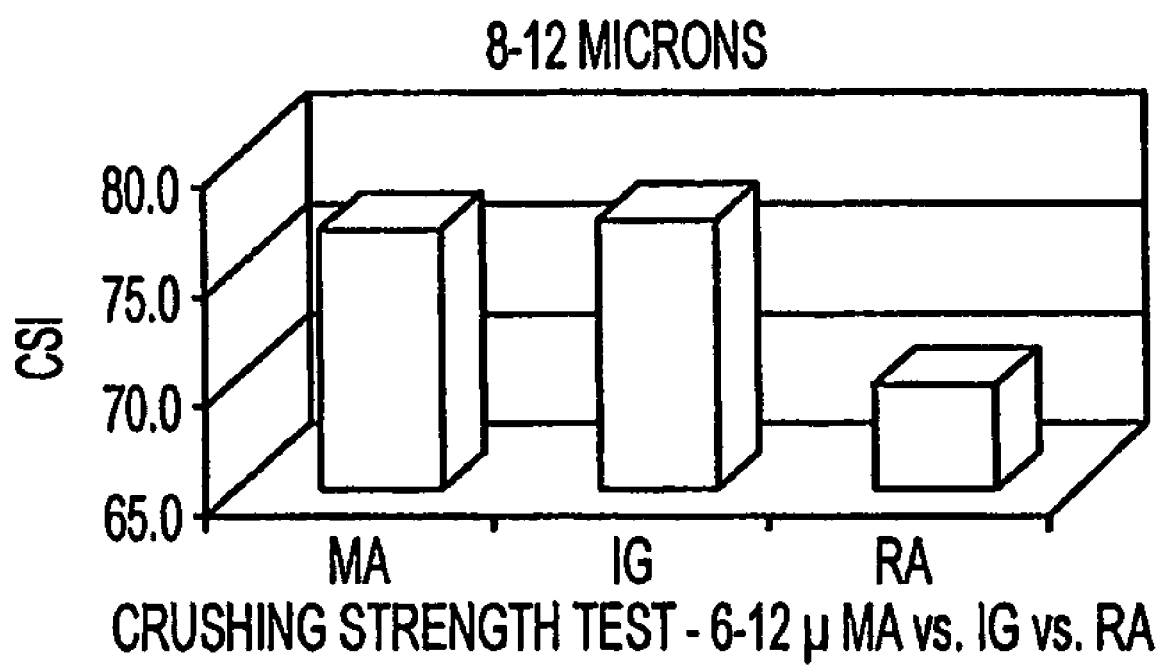

The results of crushing strength tests on several different micron superabrasive powder types/products will now be presented below and with reference to FIGS. 4 to 6:

EXAMPLE 1 (SEE FIG. 4)

Crushing Strength Index (CSI) Of 10-20 Microns MA Vs. IG Vs. RA

Test conditions:
 Load=13.4 lb;
 Cup rotation speed=10 rpm;
 Head rotation speed=10 rpm;
 Crushing time=30 sec Results:

| Type/Product | CSI |
| --- | --- |
| MA | 54.3 |
| IG | 52.5 |
| RA | 40.7 |

EXAMPLE 2 (SEE FIG. 5)

Crushing Strength Index (CSI) Of 10-20 Microns MA Vs. IG Vs. RA

Test conditions:
 Load=13.4 lb;
 Cup rotation speed=10 rpm;
 Head rotation speed=10 rpm;
 Crushing time=60 sec Results:

| Type/Product | CSI |
| --- | --- |
| MA | 51.4 |
| IG | 43.4 |
| RA | 45.6 |

TABLE 5

Crushing strength measurement precision - 10-20 μMA

| | Ref. | #1 | #2 | #3 | #4 | #5 | Mean | St. Dev. |
| --- | --- | --- | --- | --- | --- | --- | --- | --- |
| 50%-95% | 44.277 | 23.351 | 21.914 | 23.146 | 22.603 | 22.881 | 22.779 | 0.500296 |
| CSI | | 52.7 | 49.5 | 52.3 | 51.0 | 51.7 | 51.4 | 1.1299 |

EXAMPLE 3 (SEE FIG. 6)

Crushing Strength Index (CSI) Of 10-20 Microns MA Vs. IG Vs. RA

Test conditions:
  Load=13.4 lb;
  Cup rotation speed=10 rpm;
  Head rotation speed=10 rpm;
  Crushing time=120 sec Results:

| Type/Product | CSI |
| --- | --- |
| MA | 76.6 |
| IG | 77.0 |
| RA | 69.9 |

The crushing strength data indicate that, under the test conditions employed, the metal bond diamond type/product synthesized via "belt press process" (MA), exhibits higher crushing strength than the resin bond diamond type/product synthesized via "opposed anvil press" process (RA), over the entire size range investigated. By contrast, the metal bond diamond type/product synthesized via "cubic press process" (IG), shows inconsistent crushing strength over the same size range and under same test conditions. While for 30 microns and 10 microns powders the crushing strength of IG is similar to MA, the crushing strength of the 15 microns IG powder is much lower than that of MA and almost equal to that of RA.

In addition to crushing strength, further information can be gathered regarding the superabrasives tested using the present invention by studying the fracture characteristics of the tested micron superabrasive powder types/products. For example, PSD charts can be produced of the fine particles fraction generated during crushing strength tests of the micron superabrasive powder types/products investigated. To complement the PSD data, SEM and FESEM micrographs may be taken.

Distinctive fracture characteristics may be discerned between micron superabrasive powder types/products from such pre- and post-crushing micrographs. For example, crushing experiments using the present invention have shown the fracture mode of MA diamond is predominantly microchipping with the generation of mostly fine diamond fragments. MA diamond particles retain most of their integrity with the resulting particles showing a tendency towards dulling of edges and corners. The resulting particle shapes are more round. On the other hand, the fracture mode of RA diamond is predominantly microfracturing with the generation of a wide range of diamond fragments. RA diamond particles show a tendency toward retaining their sharpness as opposed to integrity—the resulting particle shapes are irregular with sharp edges and points. When comparing IG to MA, 30 microns and 10 microns IG diamond powders show more microchipping than MA (larger amount of finer diamond fragments). However, the 15 microns IG diamond powder exhibits a rather peculiar fracture mode with a combination of microchipping and microfracturing, indicating that IG diamond powder tested is a rather inconsistent type/product.

Currently, a plethora of micron superabrasive types and products is available on the market, having one common parameter: sub-sieve size. The present invention enables producers to measure the fracture strength of different micron superabrasive powders (diamond and CBN) to better control the mechanical strength of their micron superabrasive types/products. The present invention also enables end users to make an informed selection of a micron type/product that performs best in their particular application, whether in loose abrasive, slurry, compound or bonded tool form, since mechanical strength and fracture characteristics are the properties that are responsible for their performance in most applications.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only one embodiment of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A method for measuring the crushing strength of an abrasive, the abrasive comprising particles, the method comprising:
  determining an initial particle size distribution for the particles;
  subjecting the abrasive to a crushing force;
  determining a post-crushing particle size distribution for the particles; and
  comparing the initial and post-crushing particle size distributions.

2. The method of claim 1, comprising determining the initial and post-crushing particle size distributions using a particle size distribution analyzer.

3. The method of claim 2, wherein the comparing step comprises comparing the cumulative percentiles of particles between 50% and 95% of the initial and post-crushing particle size distributions.

4. The method of claim 1, wherein subjecting the abrasive to a crushing force comprises:
  placing the abrasive into a cup;
  placing a piston into the cup until a face of the piston touches the abrasive;
  applying a force to the piston or the cup such that the force is transmitted to the abrasive; and
  rotating the piston and the cup in opposite directions while the force is transmitted to the abrasive.

5. The method of claim 4, wherein the cup and the piston are rotated at a speed of about 200 RPM or less.

6. The method of claim 4, wherein the abrasive is for use in a lapping process, the method comprising subjecting the abrasive to a crushing force approximately equal to that of the lapping process.

7. The method of claim 3, wherein the comparing step comprises determining a crushing strength of the abrasive by calculating a ratio of cumulative percentiles of particles between 50% and 95% of the post-crushing particle size distribution to the cumulative percentiles of particles between 50% and 95% of the initial particle size distribution.

8. The method of claim 3, comprising determining a crushing strength index by dividing the cumulative percentiles of particles between 50% and 95% of the post-crushing particle size distribution by the cumulative percentiles of particles between 50% and 95% of the initial particle size distribution, and multiplying the result by 100.

9. The method of claim 6, wherein the abrasive comprises diamond particles having a size of about 40 microns or less, the method comprising rotating the cup and the piston at about 10 RPM, respectively;

wherein the force on the abrasive is about 13.4 lbs.

10. The method of claim 1, comprising taking initial and post-crushing micrographs of the abrasive, and comparing the micrographs to determine fracture characteristics of the abrasive.

11. The method of claim 10, comprising taking the micrographs using an SEM or FESEM.

12. An apparatus for measuring the crushing strength of an abrasive used in a lapping process, the abrasive comprising particles, the apparatus comprising:
   a cup for holding the abrasive;
   a first motor for rotating the cup in a first direction;
   a piston having a face for rotatably fitting within the cup and contacting the abrasive;
   a second motor for rotating the piston in a second direction opposite the first direction; and
   a press for pressing the piston against the abrasive and crushing the particles while the first and second motors are rotating.

13. The apparatus of claim 12, wherein the piston face and the cup each have a polycrystalline diamond compact (PCD) disc for contacting the abrasive and for preventing contact between the abrasive and the piston face and between the abrasive and the cup.

14. The apparatus of claim 12, wherein the press comprises a linear actuator for placing a load on the piston.

15. The apparatus of claim 14, further comprising:
   a base;
   a spindle rotatably mounted to the base and operatively connected to the first motor, the cup being mounted to the spindle; and
   a platform mounted to the base for supporting the piston, the linear actuator and the second motor.

16. The apparatus of claim 14, comprising a belt for connecting the spindle to the first motor.

17. The apparatus of claim 12, wherein the first and second motors are for rotating the piston and the cup, respectively, at a speed of about 200 RPM or less.

18. The apparatus of claim 12, wherein the press is for pressing the piston against the abrasive with a load of about 500 lbs or less.

19. The apparatus of claim 14, wherein the linear actuator comprises a pneumatic cylinder or a hydraulic cylinder.

20. The apparatus of claim 14, wherein the linear actuator comprises a servo driven actuator.

* * * * *